United States Patent [19]

Walker

[11] 4,155,745

[45] May 22, 1979

[54] CERTAIN 2-(CHLOROACETYLAMINO)METHYL-1,3-DIOXOLANES, THIOXALANES OR DITHIOLANES AS HERBICIDES

[75] Inventor: Francis H. Walker, Mill Valley, Calif.

[73] Assignee: Stauffer Chemical Company, Westport, Conn.

[21] Appl. No.: 893,215

[22] Filed: Apr. 4, 1978

[51] Int. Cl.² ............................................. A01N 9/00
[52] U.S. Cl. .......................................... 71/88; 71/90; 260/327 M; 260/340.9 R; 260/561 HL
[58] Field of Search ............... 260/340.9 R, 327 M; 71/88, 90

[56] References Cited

U.S. PATENT DOCUMENTS

| | | | |
|---|---|---|---|
| 2,929,702 | 3/1960 | Speziale | 71/88 |
| 3,133,808 | 5/1964 | Hamm | 71/88 |
| 4,021,224 | 5/1977 | Pallos et al. | 71/88 |
| 4,053,297 | 10/1977 | Richter | 71/88 |

Primary Examiner—Ethel G. Love
Attorney, Agent, or Firm—Edwin H. Baker

[57] ABSTRACT

Compounds having the following structural formula

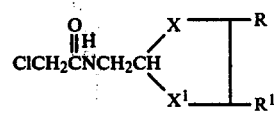

wherein R and R¹ independently are alkyl, haloalkyl, phenyl, or hydrogen; X is oxygen or sulfur; and X¹ is oxygen or sulfur which are useful as herbicides.

15 Claims, No Drawings

CERTAIN 2-(CHLOROACETYLAMINO)METHYL-1,3-DIOXOLANES, THIOXALANES OR DITHIOLANES AS HERBICIDES

BACKGROUND OF THE INVENTION

This invention relates to certain novel 2-(chloroacetylamino)methyl-1,3-dioxolanes, thioxalanes or dithiolanes which are useful as herbicides.

DESCRIPTION OF THE INVENTION

The compounds of this invention have the following structural formula $$ClCH_2\overset{\overset{O}{\|}}{C}\overset{H}{N}CH_2CH\diagdown_{X^1\!\!-\!\!-\!\!-\!\!-\!\!CH-R^1}^{X-\!\!-\!\!-\!\!-\!\!-\!\!CH-R}$$

wherein R and $R^1$ independently are:

(a) alkyl having 1 to 4 carbon atoms, preferably 1 to 2 carbon atoms (b) haloalkyl having 1 to 4 carbon atoms, preferably chloroalkyl having 1 to 2 carbon atoms (c) phenyl or (d) hydrogen, most preferably hydrogen X is oxygen or sulfur and $X^1$ is oxygen or sulfur, most preferably X and $X^1$ are oxygen.

In the above description of the compounds of this invention, alkyl includes both straight and branched chain configurations, for example, methyl, ethyl, n-propyl, isopropyl, n-butyl, sec-butyl, or tert.-butyl. The terms halo include chlorine, bromine, iodine and fluorine.

The compounds of this invention are active herbicides of a general type. That is, they are herbicidally effective against a wide range of plant species. The method of controlling undesired vegetation of the present invention comprises applying a herbicidally effective amount of the above-described compounds to the area where control is desired.

The compounds of the present invention are prepared by the following general method.

Reaction No. 1

$$ClCH_2-\overset{\overset{O}{\|}}{C}-Cl + H_2NCH_2(OCH_3)_2 + NaOH \longrightarrow$$

$$ClCH_2\overset{\overset{O}{\|}}{C}-\overset{H}{N}CH_2CH(OCH_3)_2 + NaCl$$

Generally, a mole amount of aminoacetaldehyde dimethyl acetal and a mole amount of sodium hydroxide as an aqueous solution are mixed in a solvent such as dichloromethane. Then a mole amount of chloroacetyl chloride is added dropwise to the mixture with stirring at 0–10° C. Thereafter the mixture is allowed to heat to room temperature and is stirred for 1 hour. The mixture is washed with water, sodium carbonate and water followed by drying and evaporation to yield the desired reaction product.

Reaction No. 2

$$ClCH_2\overset{\overset{O}{\|}}{C}-\overset{H}{N}CH_2CH\diagdown_{OCH_3}^{OCH_3} + \overset{HX-\!\!-\!\!-CH-R}{\underset{HX^1\!\!-\!\!-\!\!-CH-R^1}{|}} \xrightarrow{\text{acid cat.}}$$

$$ClCH_2\overset{\overset{O}{\|}}{C}\overset{H}{N}CH_2CH\diagdown_{X^1\!\!-\!\!-\!\!-CH-R^1}^{X-\!\!-\!\!-CH-R} + 2CH_3OH$$

wherein R, $R^1$, X and $X^1$ are as previously defined.

Generally, a mole amount of the amide reaction product of Reaction No. 1, a mole amount of ethylene glycol and about 0.2 mole of a strong acid catalyst such as 2-naphthalene-sulfonic acid dihydrate are dissolved in a solvent such as dichloroethane, mixed in a reaction vessel fitted with a variable tape-off distillation head attached to the column. The reaction mixture is heated to reflux with stirring and the distillate is removed at its boiling temperature around 83° C.

The reaction mixture is then cooled to room temperature and washed for 15 minutes with a potassium carbonate solution. The mixture is then filtered and the filtrate passed through a small amount of Florisil ®. The filtrate is evaporated to yield the desired reaction product.

Preparation of the compounds of this invention is illustrated by the following examples.

EXAMPLE I

N-(2,2-Dimethoxyethyl)chloroacetamide

This example teaches a method of preparation for the reactant N-(2,2-dimethoxyethyl)chloroacetamide.

A mixture of 105.1 grams (g) (1.0 moles) of aminoacetaldehyde dimethyl acetal, 80 g (1.0 moles) of a 50% aqueous solution of sodium hydroxide, and 200 ml dichloromethane are placed in a 1 liter flask fitted with a stirrer and thermometer. To this is added 113.0 g (1.0 moles) of chloroacetyl chloride dropwise with rapid stirring at 0°–10° C. After the addition is complete, the reaction is allowed to rise to room temperature and is stirred for 1 hour. Next the mixture is washed with 100 ml water, 100 ml sodium carbonate solution and 100 ml water, followed by drying and evaporation to give 113.8 g (63% yield) of the title compound, m.p. 33°–36° C.

EXAMPLE II 2-(Chloroacetylamino)methyl-1-1,3-dioxolane

This example teaches the preparation of a representative compound of the instant invention.

A mixture of 36.0 g (0.2 mole) of N-(2,2-dimethoxyethyl)chloroacetamide, 12.4 g (0.2 mole) of ethylene glycol and 0.2 g of 2-naphthalene sulfonic acid dihydrate in 150 ml dichloroethane are placed in a 500 ml flask to which a variable tape-off distillation head, the thermometer and stirrer are attached. The mixture is heated to reflux and the distillate is removed at a head temperature of 83° C. A total of 54.1 g of distillate is collected. The mixture is then cooled to room temperature and then stirred for 15 minutes with 10 grams of solid potassium carbonate. The mixture is next filtered and the filtrate passed through a small amount of Florisil ®. The filtrate is then evaporated to leave a liquid, 26.2 g (73% yield) $n_D^{30}$-1.4921, identified as the title compound by nuclear magnetic resonance.

The following is a table of certain selected compounds that are preparable according to the procedure described hereto. Compound numbers are assigned to each compound and are used throughout the remainder of the specification.

TABLE I $$ClCH_2\overset{O}{\overset{\|}{C}}-\overset{H}{N}CH_2CH\begin{array}{c}X-R\\X^1-R^1\end{array}$$

| Compound Number | X | X¹ | R | R¹ | $n_D^{30}$ (m.p.) |
|---|---|---|---|---|---|
| 1[a] | O | O | H | H | 1.4921 |
| 2 | S | S | H | H | (73°–78° C.) |
| 3 | O | S | H | H | (54°–56° C.) |
| 4 | O | O | CH₃— | H | 1.4828 |
| 5 | S | S | C₂H₅— | H | 1.5647 |
| 6 | O | O | CH₃— | CH₃— | 1.4815 |
| 7 | O | O | ClCH₂— | H— | 1.5092 |
| 8 | O | O | ⟨phenyl⟩ | H | 1.5448 |
| 9 | S | S | CH₃ | H | 1.5736 |

[a] prepared in Example II

HERBICIDAL SCREENING TESTS

As previously mentioned, the herein described compounds produced in the above-described manner are phytotoxic compounds which are useful and valuable in controlling various plant species. Selected compounds of this invention are tested as herbicides in the following manner.

Pre-emergence herbicide test. On the day preceding treatment, seeds of seven different weed species are planted in individual rows using one species per row across the width of the flat. The seeds used are hairy crabgrass (*Digitaris sanguinalis*), yellow foxtail (*Setaria glauca*), watergrass (*Echinochloa crusgalli*), California red oat (*Avena sativa*), redroot pigweed (*Amaranthus retroflexus*), Indian mustard (*Brassica juncea*) and curly dock (*Rumex crispus*). Ample seeds are planted to give about 20 to 50 seedlings per row, after emergence, depending upon the size of the plants. The flats are watered after planting. Using an analytical balance, 20 ml. of the compound to be tested was weighed out on a piece of glassine weighing paper. The paper and compound were placed in a 30 ml. wide-mouth bottle and 3 ml. of acetone containing 1% polyoxyethylene sorbitan monolaurate emulsifier was added to dissolve the compound. If the material was not soluble in acetone, another solvent such as water, alcohol or dimethylformamide (DMF) was used instead. When DMF was used, only 0.5 ml. or less was used to dissolve the compound and then another solvent was used to make the volume up to 3 ml. The 3 ml. solution was sprayed uniformly on the soil contained in a small flat 7 inches long, 5 inches wide and 2.75 inches deep, one day after planting weed seeds in the flat of soil. A No. 152 DeVilbiss atomizer was used to apply the spray using compressed air at a pressure of 5 lb/sq. inch. The rate of application was 8 lb/acre and the spray volume was 143 gallon/acre.

After treatment, the flats were placed in the greenhouse at a temperature of 70° to 85° F. and watered by sprinkling. Two weeks after treatment the degree of injury or control was determined by comparison with untreated check plants of the same age. The injury rating from 0 to 100% was recorded for each species as percent control with 0% representing no injury and 100% representing complete control.

Post-emergence herbicide test. Seeds of six plant species, including hairy crabgrass, watergrass, red oat, mustard, curly dock and pinto beans (*Phaseolus vulgaris*) were planted in the flats as described above for pre-emergence screening. The flats were placed in the greenhouse at 70° to 85° F. and watered daily with a sprinkler. About 10 to 14 days after planting, when the primary leaves of the bean plants were almost fully expanded and the first trifoliate leaves were just starting to form, the plants were sprayed. The spray was prepared by weighing out 20 ml. of the test compound, dissolving it in 2.5 ml. of acetone containing 1% polyoxyethylene sorbitan monolaurate and then adding 2.5 ml. of water. The solution was sprayed on the foliage using a No. 152 DeVilbiss atomizer at an air pressure of 5 lb/sq. inch. The spray concentration was 0.2% and the rate is 8 lb/acre. The spray volume was 238 gallon/acre.

The injury rating is from 0 to 100% as described above for the pre-emergence herbicide screening test.

The results of these tests are shown in the following Table 2.

TABLE 2

| Compound | Pre-emergence control | Post-emergence control |
|---|---|---|
| 1 | 63 | 42 |
| 2 | 44 | 60 |
| 3 | 55 | 61 |
| 4 | 88 | 72 |
| 5 | 28 | 23 |
| 6 | 49 | 41 |
| 7 | 95 | 52 |
| 8 | 63 | 30 |
| 9 | 45 | 30 |

The compounds of the present invention are used as pre-emergence or post-emergence herbicides and are applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for both pre-. and post-emergence herbicidal applications are wettable powders, emulsifiable concentrates and granules. These formulations may contain as little as about 0.5% to as much as about 95% or more by weight of active ingredient. A herbicidally effective amount depends upon the nature of the seeds or plants to be controlled and the rate of application varies from about 0.05 to approximately 25 pounds per acre, preferably from about 0.1 to 10 pounds per acre.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5% to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthal, isophorone and other nonvolatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5% to 95% of active by weight of the herbicidal composition.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5% to about 25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1% to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely-divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to convention methods and are distributed in the soil to a depth of at least ½ inch below the soil surface. It is not necessary that the phytotoxic compositions be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvant or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-s-triazine, 2-chloro-4-ethylamino-6-isopropylamino-s-triazine, and 2-ethylamino-4-isopropylamino-6-methylmercapto-s-triazine; urea derivatives, such as 3-(3,4-dichlorophenyl)-1,1-dimethyl urea and 3-(p-chlorophenyl)-1,1-dimethyl urea; and acetamides such as N,N-diallyl-α-chloroacetamide, and the like; benzoic acids such as 3-amino-2,5-dichlorobenzoic; thiocarbamates, such as S-propyl dipropylthiocarbamate, S-ethyl-dipropylthiocarbamate, S-ethyl cyclohexylethyl thiocarbamate, S-ethyl hexahydro-1H-azepine-1-carbothioate and the like; 4-(methylsulfonyl)-2,6-dinitro-N,N-substituted anilines, such as 4-(methylsulfonyl)-2,6-dinitro-N,N-substituted anilines, such as 4-trifluoromethyl-2,6-dinitro-N,N-di-n-propyl aniline and 4-trifluoromethyl-2,6-dinitro-N-ethyl-N-n-butyl aniline. Fertilizers useful in combination with the active ingredients include, for example, ammonium nitrate, urea and superphosphate. Other useful additaments include materials in which plant organisms take root and grow such as compost, manure, humus, sand and the like.

What is claimed is:

1. Compounds of the following structural formula

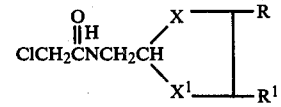

wherein R and R[1] independently are:
 (a) alkyl having 1 to 4 carbon atoms,
 (b) haloalkyl having 1 to 4 carbon atoms,
 (c) phenyl or
 (d) hydrogen X is oxygen or sulfur, and X[1] is oxygen or sulfur.

2. The compound of claim 1 wherein R and R[1] independently are alkyl having 1 to 2 carbon atoms, chloroalkyl having 1 to 2 carbon atoms, phenyl or hydrogen, X is oxygen and X[1] is oxygen.

3. The compound of claim 1 wherein R is hydrogen, R[1] is hydrogen, X is oxygen and X[1] is oxygen.

4. The compound of claim 1 wherein R is hydrogen, $R^1$ is hydrogen, X is oxygen and $X^1$ is sulfur.

5. The compound of claim 1 wherein R is methyl, $R^1$ is hydrogen, X is oxygen, and $X^1$ is oxygen.

6. The compound of claim 1 wherein R is chloromethyl, $R^1$ is hydrogen, X is oxygen and $X^1$ is oxygen.

7. The compound of claim 1 wherein R is phenyl, $R^1$ is hydrogen, X is oxygen and $X^1$ is oxygen.

8. The method of controlling undesirable vegetation which comprises applying to the area where control of said vegetative growth is desired, an herbicidally effective amount of a compound of the following structural formula

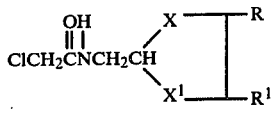

wherein R and $R^1$ independently are:
 (a) alkyl having 1 to 4 carbon atoms,
 (b) haloalkyl having 1 to 4 carbon atoms
 (c) phenyl, or
 (d) hydrogen X is oxygen or sulfur, and $X^1$ is oxygen or sulfur.

9. The method of claim 8 wherein R and $R^1$ independently are alkyl having 1 to 2 carbon atoms, chloroalkyl having 1 to 2 carbon atoms, phenyl or hydrogen, X is oxygen and $X^1$ is oxygen.

10. The method of claim 8 wherein R is hydrogen, $R^1$ is hydrogen, X is oxygen and $X^1$ is oxygen.

11. The method of claim 8 wherein R is hydrogen, $R^1$ is hydrogen, X is oxygen and $X^1$ is sulfur.

12. The method of claim 8 wherein R is methyl, $R^1$ is hydrogen, X is oxygen, and $X^1$ is oxygen.

13. The method of claim 8 wherein R is chloromethyl, $R^1$ is hydrogen, X is oxygen and $X^1$ is oxygen.

14. The method of claim 8 wherein R is phenyl, $R^1$ is hydrogen, X is oxygen and $X^1$ is oxygen.

15. The herbicidal composition of matter comprising a herbicidally effective amount of the compound having the structural formula

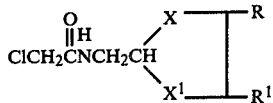

wherein R and $R^1$ independently are:
 (a) alkyl having 1 to 4 carbon atoms,
 (b) haloalkyl having 1 to 4 carbon atoms,
 (c) phenyl, or
 (d) hydrogen, X is oxygen or sulfur, and $X^1$ is oxygen or sulfur, and an inert carrier.

* * * * *